United States Patent [19]
Müller et al.

[11] Patent Number: 5,834,481
[45] Date of Patent: Nov. 10, 1998

[54] HETEROTRICYCLICALLY SUBSTITUTED PHENYL-CYCLOHEXANE-CARBOXYLIC ACID DERIVATIVES

[75] Inventors: Ulrich E. Müller, Wuppertal; Jürgen Dressel, Radevormwald; Peter Fey, Wuppertal; Rudolf H. Hanko, Düsseldorf; Walter Hübsch; Thomas Krämer, both of Wuppertal; Matthias Müller-Gliemann, Solingen; Martin Beuck, Erkrath; Stanislav Kazda, Wuppertal; Stefan Wohlfeil, Hilden; Andreas Knorr, Ekrath; Johannes-Peter Stasch, Solingen; Siegfried Zaiss, Wuppertal, all of Germany

[73] Assignee: Bayer Aktiengesellschaft, Leverkusen, Germany

[21] Appl. No.: 889,683

[22] Filed: Jul. 8, 1997

Related U.S. Application Data

[62] Division of Ser. No. 525,933, Sep. 8, 1995, Pat. No. 5,708,003, which is a division of Ser. No. 212,609, Mar. 11, 1994, Pat. No. 5,478,836.

[30] Foreign Application Priority Data

Mar. 18, 1993 [DE] Germany ............... 43 08 788.4

[51] Int. Cl.$^6$ ............ C07D 209/82; C07D 209/94; C07D 471/04; A61K 31/44
[52] U.S. Cl. ............ 514/292; 514/411; 546/84; 546/86; 546/87; 548/439
[58] Field of Search ............... 546/85, 86, 87, 546/84; 514/292, 411; 548/439

[56] References Cited

U.S. PATENT DOCUMENTS

| | | | |
|---|---|---|---|
| 3,632,807 | 1/1972 | Maurer et al. | 546/345 |
| 4,719,211 | 1/1988 | Abou-Gharbia et al. | 514/253 |
| 5,212,195 | 5/1993 | Clark et al. | 514/381 |

FOREIGN PATENT DOCUMENTS

| | | |
|---|---|---|
| 0217737 | 4/1987 | European Pat. Off. . |
| 0218541 | 4/1987 | European Pat. Off. . |
| 0249301 | 12/1987 | European Pat. Off. . |
| 0253310 | 1/1988 | European Pat. Off. . |
| 0324377 | 7/1989 | European Pat. Off. . |
| 0399731 | 11/1990 | European Pat. Off. . |
| 0399732 | 11/1990 | European Pat. Off. . |
| 0407102 | 1/1991 | European Pat. Off. . |
| 0497516 | 8/1992 | European Pat. Off. . |
| 0511791 | 11/1992 | European Pat. Off. . |

OTHER PUBLICATIONS

Eur. J. Med. Chem.—Chimica Therapeutica, Nov.–Dec., 1976, vol. 11, No. 6, pp. 493–499; "Antiinflammatoires dérivés de l'acide phénylacétique . . ." M. Langlois et al.
The Journal of Cell Biology, vol. 50, 1971, pp. 172–186.

*Primary Examiner*—Alan L. Rotman
*Attorney, Agent, or Firm*—Sprung Kramer Schaefer & Briscoe

[57] ABSTRACT

Heterotricyclically substituted phenyl-cyclohexanecarboxylic acid derivatives are prepared by reacting the heterocyclic compounds with cyclohexanecarboxylic acid derivatives which are substituted by benzyl halide radicals. The compounds can be employed as active compounds in medicaments.

18 Claims, No Drawings

HETEROTRICYCLICALLY SUBSTITUTED PHENYL-CYCLOHEXANE-CARBOXYLIC ACID DERIVATIVES

This is a division of application Ser. No. 08/525,933, filed on Sep. 8, 1995, U.S. Pat. No. 5,708,003, which is a divisional of application Ser. No. 08/212,609, filed on Mar. 11, 1994, now U.S. Pat. No. 5,478,836.

The invention relates to heterotricyclically substituted phenyl-cyclohexane-carboxylic acid derivatives, a process for their preparation and their use in medicaments, in particular as hypotensive and antiatherosclerotic agents.

It is known that renin, a proteolytic enzyme, eliminates the decapeptide angiotensin I in vivo from angiotensinogen, and the angiotensin I is in turn degraded in the lungs, the kidneys or other tissues to the hypertensive octapeptide angiotensin II. The various effects of angiotensin II, such as, for example, vasoconstriction, $Na^+$ retention in the kidney, aldosterone release in the adrenal gland and increase in tone of the sympathetic nervous system act synergistically in the sense of a blood pressure increase.

Moreover, angiotensin II has the property of promoting the growth and the replication of cells such as, for example, cardiac muscle cells and smooth muscle cells, these growing and proliferating at an increased rate in various disease states (for example hypertension, atherosclerosis and cardiac insufficiency).

In addition to the inhibition of renin activity, a possible starting point for intervention in the reninangiotensin system (RAS) is the inhibition of the activity of angiotensin-converting enzyme (ACE) and the blockage of angiotensin II receptors.

In addition, heterocyclic compounds having A II-antagonistic action are disclosed in EP 407 102, EP 399 731, EP 399 732, EP 324 377 and EP 253 310.

The present invention relates to heterotricyclically substituted phenyl-cyclohexane-carboxylic acid derivatives of the general formula (I)

in which

A and B together form a radical of the formula

D and E together form a radical of the formula in which $R^1$, $R^2$ and $R^3$ are identical or different and denote hydrogen or aryl having 6 to 10 carbon atoms, which is optionally substituted by hydroxyl, halogen or trifluoromethyl or by straight-chain or branched alkyl or alkoxy in each case having up to 6 carbon atoms, or denote straight-chain or branched alkyl or alkenyl in each case having up to 8 carbon atoms, or denote cycloalkyl having 3 to 8 carbon atoms, or denote halogen, L represents hydrogen, halogen, nitro, hydroxyl, trifluoromethyl, trifluoromethoxy, straight-chain or branched alkyl, alkoxy or alkoxycarbonyl in each case having up to 6 carbon atoms, cyano or carboxyl, T represents a radical of the formula $$-CO_2R^4, \quad -CO-NR^5SO_2R^6 \quad \text{or} \quad -CO-NR_7\overset{R_8}{\underset{}{\diagup}}R_9,$$

in which $R^4$ denotes hydrogen, straight-chain or branched alkyl having up to 8 carbon atoms, cycloalkyl having 3 to 7 carbon atoms or phenyl, $R^5$ and $R^7$ are identical or different and denote hydrogen or straight-chain or branched alkyl having up to 6 carbon atoms, $R^6$ denotes trifluoromethyl or straight-chain or branched alkyl having up to 6 carbon atoms, or benzyl or phenyl, each of which is optionally substituted by straight-chain alkyl having up to 6 carbon atoms, $R^8$ denotes aryl having 6 to 10 carbon atoms, which is optionally substituted up to 2 times by identical or different substituents from the group consisting of halogen, hydroxyl, straight-chain or branched alkyl, alkoxy or alkoxycarbonyl in each case having up to 6 carbon atoms, carboxyl, phenoxy and $C_3$–$C_6$,-cycloalkoxy, $R^9$ denotes a group of the formula $-CH_2-OR^{10}$, $-CO_2R^{11}$, $-CO-NR^{12}R^{13}$ or pyridyl, in which $R^{10}$ denotes hydrogen or straight-chain or branched alkyl having up to 8 carbon atoms, $R^{11}$ denotes hydrogen, straight-chain or branched alkyl having up to 8 carbon atoms, or phenyl or cycloalkyl having 3 to 6 carbon atoms, $R^{12}$ and $R^{13}$ are identical or different and denote hydrogen, straight-chain or branched alkyl having up to 8 carbon atoms, or phenyl, or T represents tetrazolyl, which is optionally substituted by straight-chain or branched alkyl having up to 4 carbon atoms or by the triphenylmethyl group, if appropriate in an isomeric form, and their salts.

The compounds of the general formula (I) according to the invention can also be present in the form of their salts. In general, salts with organic or inorganic bases or acids may be mentioned here.

In the context of the present invention, physiologically acceptable salts are preferred. Physiologically acceptable salts of the new heterotricyclically substituted phenyl-cyclohexane-1-carboxylic acids and -carboxylic acid derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, and also ammonium salts which are derived from ammonia, or organic amines such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms which behave either as image and mirror image (enantiomers), or which do not behave as image and mirror image (diastereomers). The invention relates both to the enantiomers or diastereomers or to their respective mixtures. Like the diastereomers, the racemic forms can be separated in a known manner into the stereoisomerically uniform constituents [cf. E.L. Eliel, Stereochemistry of Carbon Compounds, McGraw Hill, 1962].

Preferred compounds of the general formula (I) are those in which

A and B together form a radical of the formula

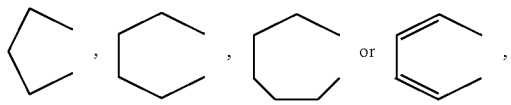

D and E together form a radical of the formula

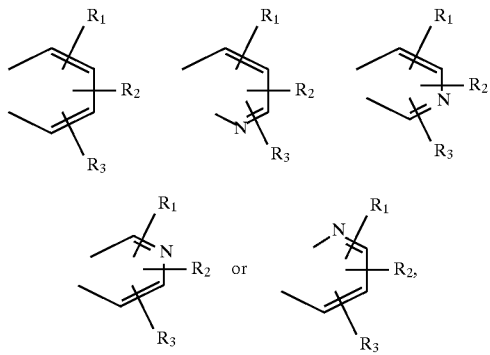

in which $R^1$, $R^2$ and $R^3$ are identical or different and denote hydrogen or phenyl which is optionally substituted by hydroxyl, fluorine, chlorine, bromine or trifluoromethyl or by straight-chain or branched alkyl or alkoxy in each case having up to 4 carbon atoms, or denote straight-chain or branched alkyl or alkenyl in each case having up to 6 carbon atoms, or denote cyclopropyl, cyclobutyl, cyclopentyl, cyclohexyl or cycloheptyl, or denote fluorine, chlorine or bromine, L represents hydrogen, fluorine, chlorine, bromine, trifluoromethyl, carboxyl or straight-chain or branched alkyl, alkoxy or alkoxycarbonyl in each case having up to 4 carbon atoms, T represents a radical of the formula

in which $R^4$ denotes hydrogen, straight-chain or branched alkyl having up to 6 carbon atoms, cyclopropyl, cyclopentyl, cyclohexyl or phenyl, $R^5$ and $R^7$ are identical or different and denote hydrogen or straight-chain or branched alkyl having up to 4 carbon atoms, $R^6$ denotes trifluoromethyl or straight-chain or branched alkyl having up to 4 carbon atoms, or benzyl or phenyl, each of which is optionally substituted by straight-chain or branched alkyl having up to 4 carbon atoms, $R^8$ denotes phenyl which is optionally substituted by fluorine, chlorine, bromine, hydroxyl, straight-chain or branched alkyl, alkoxy or alkoxycarbonyl in each case having up to 4 carbon atoms, carboxyl or phenoxy, $R^9$ denotes a group of the formula $-CH_2-OR^{10}$, $-CO_2R^{11}$, $-CO-NR^{12}R^{13}$ or pyridyl, in which $R^{10}$ denotes hydrogen or straight-chain or branched alkyl having up to 6 carbon atoms, $R^{11}$ denotes hydrogen, straight-chain or branched alkyl having up to 6 carbon atoms, phenyl, cyclopropyl, cyclopentyl or cyclohexyl, $R^{12}$ and $R^{13}$ are identical or different and denote hydrogen, straight-chain or branched alkyl having up to 6 carbon atoms, cyclopropyl, cyclopentyl, cyclohexyl or phenyl, or T represents tetrazolyl, which is optionally substituted by methyl or the triphenylmethyl group, if appropriate in an isomeric form, and their salts.

Particularly preferred compounds of the general formula (I) are those in which

A and B together form a radical of the formula

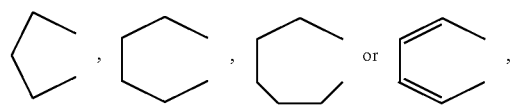

D and E together form a radical of the formula

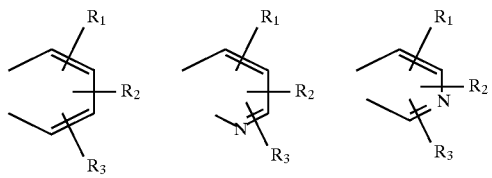

in which

R¹, R² and R³ are identical or different and denote hydrogen, methyl, fluorine, chlorine or bromine, L represents hydrogen, fluorine, chlorine, bromine, trifluoromethyl, trifluoromethoxy or methyl, T represents a radical of the formula

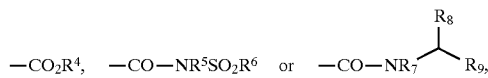

in which

R4 denotes hydrogen or straight-chain or branched alkyl having up to 4 carbon atoms, cyclopropyl, cyclopentyl, cyclohexyl or phenyl, R⁵ and R⁷ are identical or different and denote hydrogen or methyl, R⁶ denotes trifluoromethyl or methyl, ethyl, benzyl, p-tolyl or phenyl, R⁸ denotes phenyl which is optionally substituted by fluorine, chlorine, bromine, hydroxyl, straight-chain or branched alkyl, alkoxy or alkoxycarbonyl in each case having up to 3 carbon atoms, carboxyl or phenoxy, R⁹ denotes a group of the formula $-CH_2-OR^{10}$, $-CO_2-R^{11}$, $-CO-NR^{12}R^{13}$ or pyridyl, in which R¹⁰ denotes hydrogen or straight-chain or branched alkyl having up to 4 carbon atoms, R¹¹ denotes hydrogen or straight-chain or branched alkyl having up to 4 carbon atoms, phenyl, cyclopropyl, cyclopentyl or cyclohexyl, R¹² and R¹³ are identical or different and denote hydrogen or straight-chain or branched alkyl having up to 4 carbon atoms, cyclopropyl, cyclopentyl, cyclohexyl or phenyl, or T represents tetrazolyl, which is optionally substituted by methyl, or the triphenylmethyl group, if appropriate in an isomeric form, and their salts.

Very particularly preferred compounds of the general formula (I) are those in which A and B together form a radical of the formula

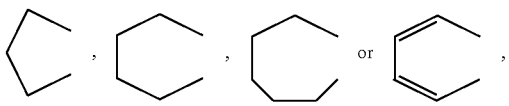

D and E together form a radical of the formula

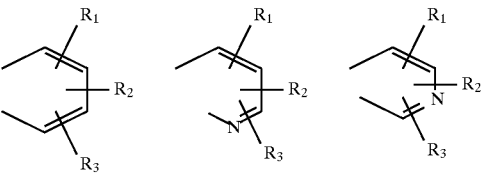

in which

R¹, R² and R³ are identical or different and denote hydrogen or methyl,

L represents hydrogen,

T represents a radical of the formula

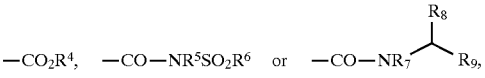

in which

R⁴ denotes hydrogen or straight-chain or branched alkyl having up to 4 carbon atoms, R⁵ and R⁷ denote hydrogen, R⁶ denotes trifluoromethyl, methyl or p-tolyl, R⁸ denotes phenyl, and R⁹ denotes a group of the formula $-CH_2OH$, or T represents tetrazolyl, which is optionally substituted by triphenylmethyl, if appropriate in an isomeric form, and their salts.

A process for the preparation of the compounds of the general formula (I) according to the invention has additionally been found, characterized in that compounds of the general formula (II)

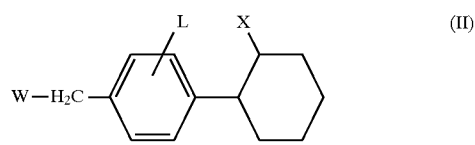

in which

L has the abovementioned meaning,

W represents a typical leaving group such as, for example, chlorine, bromine, iodine, tosylate or mesylate, preferably bromine and X represents $C_1-C_6$-alkoxycarbonyl or the triphenylmethyl-tetrazol-1-yl group, are reacted first with compounds of the general formula (III)

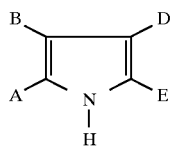

in which

A, B, D and E have the abovementioned meaning, in inert solvents, if appropriate in the presence of a base and if appropriate under a protective gas atmosphere, to give compounds of the general formula (IV)

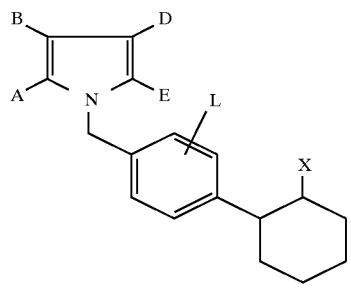

in which

A, B, D, E, L and X have the abovementioned meaning, and if appropriate starting from the corresponding carboxylic acids, after prior hydrolysis and/or activation, the products are subsequently amidated or sulphonamidated in inert solvents with sulphonamides or amines of the general formulae (V) and (Va)

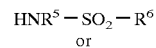

or

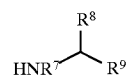

in which $R^5$, $R^6$, $R^7$, $R^8$ and $R^9$ have the abovementioned meaning, if appropriate in the presence of a base and/or of an auxiliary, for example of a dehydrating agent, and in the case of the free tetrazoles, if appropriate the triphenylmethyl group is removed by customary methods using acids, preferably using trifluoroacetic acid or hydrochloric acid in dioxane, and if appropriate the isomers are separated, and in the case of the preparation of the salts reacted with an appropriate base or acid.

The process according to the invention can be illustrated by way of example by the following reaction scheme:

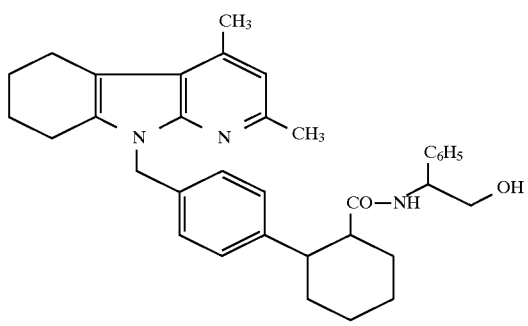
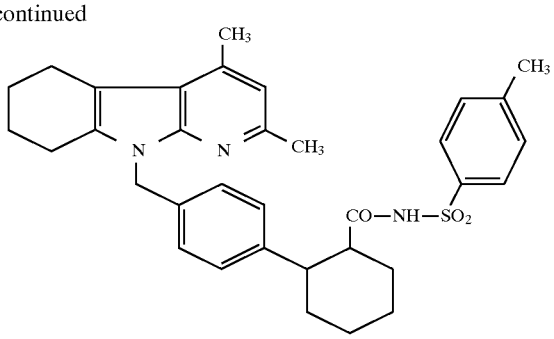

Suitable solvents for the process are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dimethylformamide and tetrahydrofuran are preferred.

Bases which can be employed for the process according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal or alkaline earth metal alkoxides such as sodium methoxide or potassium methoxide, sodium ethoxide or potassium ethoxide or potassium tert-butoxide, or organic amines (trialkyl ($C_1$—$C_6$) amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methsylpiperidine or morpholine. It is also possible to employ as bases alkali metals such as sodium or their hydrides such as sodium hydride. Sodium hydride, potassium carbonate, triethylamine, pyridine and potassium tert-butoxide, DBU or DABCO are preferred.

In general, the base is employed in an amount from 0.05 mol to 10 mol, preferably from 1 mol to 2 mol, relative to 1 mol of the compound of the formula (III).

The process according to the invention is in general carried out in a temperature range from −30° C. to +100° C., preferably from −10° C. to +60° C.

The process according to the invention is in general carried out at normal pressure. However, it is also possible to carry out the process at elevated pressure or at reduced pressure (for example in a range from 0.5 to 5bar).

Suitable bases for the hydrolysis are the customary inorganic bases. These preferably include alkali metal hydroxides or alkaline earth metal hydroxides such as, for example, lithium hydroxide, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert-butoxide. Lithium hydroxide, sodium hydroxide or potassium hydroxide is particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide, or dimethyl sulphoxide. Alcohols such as methanol, ethanol, propanol or isopropanol are particularly preferably used. It is also possible to employ mixtures of the solvents mentioned.

The hydrolysis can also be carried out using aqueous acids such as, for example, trifluoroacetic acid, acetic acid, hydrochloric acid, hydrobromic acid, methanesulphonic acid, sulphuric acid or perchloric acid, preferably using trifluoroacetic acid.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

When carrying out the reaction, the carboxylates of the compounds according to the invention are formed in the first step as intermediates which can be isolated. The acids according to the invention are obtained by treating the carboxylates with customary inorganic acids. These preferably include acids such as, for example, hydrochloric acid, hydrobromic acid, sulphuric acid, phosphoric acid or trifluoroacetic acid. It has proven advantageous in this case in the preparation of the carboxylic acids to acidify the basic reaction mixture from the hydrolysis in a second step without isolation of the carboxylates. The acids can then be isolated in a customary manner. In the case of the basic heterocycles, the salts of the heterocycles with the inorganic acids can also be obtained by treating the solutions of the carboxylates with the abovementioned acids.

The amidation of the compounds of the general formula (IV) is in general carried out in one of the abovementioned solvents, preferably in tetrahydrofuran or dichloromethane.

The amidation can optionally take place via the activated stage of the acid halides [(IV) Y=halogen], which can be prepared from the appropriate acids by reaction with thionyl chloride, phosphorus trichloride, phosphorus pentachloride, phosphorus tribromide or oxalyl chloride.

The amidation is in general carried out in a temperature range from −80° C. to +80° C., preferably from −30° C. to +30° C., and at normal pressure.

Suitable bases for this in addition to the abovementioned bases are preferably triethylamine and/or dimethylaminopyridine, DBU or DABCO.

The base is employed in an amount from 0.5 mol to 10 mol, preferably from 1 mol to 5 mol, relative to 1 mol of the compounds of the general formulae (IV) and (V).

Acid-binding agents which can be employed for the amidation are alkali metal or alkaline earth metal carbonates such as sodium carbonate, potassium carbonate, alkali metal or alkaline earth metal hydroxides such as, for example, sodium hydroxide or potassium hydroxide, or organic bases such as pyridine, triethylamine or N-methylpiperidine, or bicyclic amidines such as 1,5-diazabicyclo[4.3.0]non-5-ene (DBN) or 1,5-diazabicyclo-[5.4.0]undec-5-ene (DBU). Potassium carbonate is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxytris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide.

The acid-binding agents and dehydrating reagents are in general employed in an amount from 0.5 to 3 mol, preferably from 1 to 1.5 mol, relative to 1 mol of the corresponding carboxylic acids.

The cyclohexane compounds of the general formula (II) are in the main new and can be prepared by converting compounds of the general formula (VI)

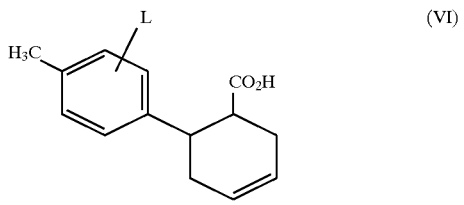

(VI)

in which

L has the abovementioned meaning, first by hydrogenation with palladium/C in one of the abovementioned solvents, preferably methanol, in a hydrogen atmosphere into the compounds of the general formula (VII)

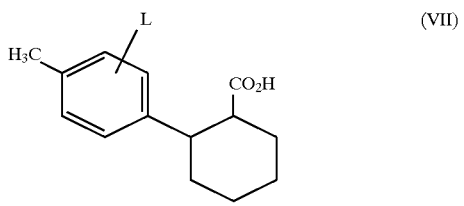

(VII)

in which

L has the abovementioned meaning, in a second step, in the case where T≠tetrazole, esterifying by customary methods, and in the case where T represents the tetrazolyl radical, reacting with chlorosulphonyl isocyanate in dichloromethane to give the corresponding cyano compounds, then introducing the tetrazolyl group using sodium azide/triethylammonium chloride, in the presence of one of the abovementioned bases, preferably N,N-dimethylformamide, under a nitrogen atmosphere, and introducing the triphenyl-methyl group by further reaction with triphenylmethyl chloride in the presence of one of the abovementioned solvents and bases, preferably dichloromethane and triethylamine, and in a last step carrying out a bromination of the methylene group, if appropriate in the presence of a catalyst.

The reduction of the double bond is carried out in a temperature range from 0° C. to +40° C., preferably at +20° C. and a pressure of 1 bar.

The esterification is carried out in one of the abovementioned solvents, preferably toluene and tetrahydrofuran, after the prior activation of the corresponding carboxylic acid which has already been described above, preferably via the carbonyl chlorides, and subsequent reaction with the corresponding alkoxides, in a temperature range from 0° C. to +60° C., preferably at +10° C. to +35° C. and at normal pressure.

The reactions to give the cyano compounds and tetrazolyl compounds are in general carried out at the boiling point of the respective solvent and at normal pressure.

The introduction of the triphenylmethyl group into the tetrazolyl ring is in general carried out at 0° C.

The bromination is in general carried out in a temperature range from +40° C. to 100° C., preferably from +60° C. to +90° C. and at normal pressure. It is carried out in one of the abovementioned solvents, preferably using carbon tetrachloride, and using N-bromosuccinimide.

A suitable starter (catalyst) for the bromination is, for example, azobisisobutyronitrile or dibenzoyl peroxide, preferably azobisisobutyronitrile, the starter being employed in an amount from 0.01 mol to 0.1 mol, preferably from 0.01 mol to 0.05 mol, relative to 1 mol of the compound of the general formula (VII).

The compounds of the general formula (VI) are also new and can be prepared, for example, by reacting compounds of the general formula (VIII)

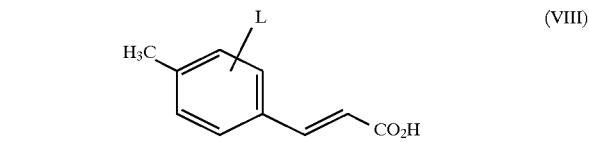

(VIII)

in which

L has the abovementioned meaning, in one of the abovementioned solvents, preferably toluene, with 1,3-butadiene in the presence of hydroquinone, in a temperature range from +180° C. to +230° C., preferably at 200° C. and pressure of about 20 bar [cf. here Eur. J. Med. Chem. 11, 493 (1976)].

The compounds of the general formula (VIII) are known per se or can be prepared by customary methods.

The compounds of the general formulae (IV) and (VII) are new and can be prepared, for example, by the processes described above.

The compounds of the general formula (III) are likewise known per se or can be prepared by a customary method.

The amines of the general formula (V) are known or can be prepared by known processes.

The compounds of the general formula (I) according to the invention exhibit an unforeseeable, useful spectrum of pharmacological action.

The compounds according to the invention have a specific A II-antagonistic action, since they competitively inhibit the binding of angiotensin II to the receptors. They suppress the vasoconstrictory and aldosterone secretion-stimulating effects of angiotensin II. They moreover inhibit the proliferation of smooth muscle cells.

They can therefore be employed in medicaments for the treatment of arterial hypertension and atherosclerosis. They can moreover be employed for the treatment of coronary heart diseases, cardiac insufficiency, brain function disorders, ischaemic cerebral diseases, peripheral circulatory disorders, functional disorders of the kidney and adrenal gland, bronchospastic diseases and diseases of the respiratory tract having a vascular component, sodium retention and oedemas.

Investigation of the inhibition of the contraction induced by agonists

Rabbits of either sex are stunned by a blow to the back of the head and exsanguinated, or in some cases anaesthetized with Nembutal (about 60–80 mg/kg i.v.) and sacrificed by opening the thorax. The thoracic aorta is removed, freed from adhering connective tissue, divided into ring segments 1.5 mm wide and individually transferred under an initial loading of about 3.5 g to 10 ml organ baths containing Krebs-Henseleit nutrient solution, temperature-controlled at 37° C. and aerated with 95% $O_2$/5% $CO_2$, of the following composition: 119 mmol/l of NaCl; 2.5 mmol/l of $CaCl_2 \times 2$ $H_2O$; 1.2 mmol/l of $KH_2PO_4$; 10 mmol/l of glucose; 4.8 mmol/l of KCl; 1.4 mmol/l of $MgSO_4 \times 7$ $H_2O$ and 25 mmol/l of $NaHCO_3$.

The contractions are determined isometrically by means of Statham UC2 cells via bridge amplifiers (ifd Mülheim or DSM Aalen) and digitalized by means of A/D converters (System 570, Keithley Munich) and assessed. The agonist dose response curves (DRCs) are plotted hourly. With each DRC, 3 or 4 individual concentrations are applied to the baths at 4 min intervals. After the end of the DRC and subsequent washing-out cycles (16 times in each case about 5 sec/min with the abovementioned nutrient solution), a 28-minute resting or incubation phase follows, within which the contractions as a rule reach the starting value again.

The height of the 3rd DRC, in a normal case, is used as a reference quantity for the assessment of the test substance to be investigated in further runs, which substance is applied to the baths in the following DRCs in each case in increasing dosage at the start of the incubation period. Each aorta ring is in this case stimulated for the whole day, always with the same agonist.

| Agonists and their standard concentrations (administration volume per individuai dose = 100 µl): | | |
|---|---|---|
| KCl | 22.7; 32.7; 42.7; 52.7 | mmol/l |
| 1-Noradrenaline | $3 \times 10^{-9}$; $3 \times 10^{-8}$; $3 \times 10^{-7}$; $3 \times 10^{-6}$; | g/ml |
| Serotonin | $10^{-8}$; $10^{-7}$; $10^{-6}$; $10^{-5}$ | g/ml |
| B-HT 920 | $10^{-7}$; $10^{-6}$; $10^{-5}$; | g/ml |
| Methoxamine | $10^{-7}$; $10^{-6}$; $10^{-5}$; | g/ml |
| Angiotensin II | $3 \times 10^{-9}$; $10^{-8}$; $3 \times 10^{-8}$; $10^{-7}$; | g/ml |

To calculate the $IC_{50}$ (concentration at which the substance to be investigated causes a 50% inhibition), the effect is in each case based on the 3rd=submaximal agonist concentration.

The compounds according to the invention inhibit the contraction of the isolated rabbit aorta induced by angiotensin II in a dose-dependent manner. The contraction induced by potassium depolarization or other agonists was not inhibited or only weakly inhibited at high concentrations.

Blood pressure measurements on the angiotensin II-infused rat

Male Wistar rats (Moellegaard, Copenhagen, Denmark) having a body weight of 300–350 g are anaesthetized with thiopental (100 mg/kg i.p.). After tracheotomy, a catheter for blood pressure measurements is inserted in the femoral artery and a catheter for angiotensin II infusion and a catheter for substance administration are inserted in the femoral veins. After administration of the ganglionic blocker pentolinium (5 mg/kg i.v.), the angiotensin II infusion (0.3 µg/kg/min) is started. As soon as the blood pressure values have reached a stable plateau, the test substances are administered either intravenously or orally as a suspension or solution in 0.5% Tylose. The blood pressure changes under the action of substance are indicated as mean values±SEM in the table.

Determination of the antihypertensive activity in conscious hypertensive rats

The oral antihypertensive activity of the compounds according to the invention was tested in conscious rats having surgically induced unilateral renal artery stenosis. To do this, the right renal artery was constricted with a silver clip of 0.18 mm internal width. In this form of hypertension, the plasma renin activity is increased in the first six weeks after intervention. The arterial blood pressure of these animals was measured in a bloodless manner at defined time intervals after substance administration using the "tail cuff". The substances to be tested were administered intragastrally ("orally") by stomach tube at various doses suspended in a Tylose suspension. The compounds according to the invention reduce the arterial blood pressure of the hypertensive rats at a clinically relevant dosage.

The compounds according to the invention additionally inhibit the specific binding of radioactive angiotensin II in a concentration-dependent manner.

Interaction of the compounds according to the invention with the angiotensin II receptor in membrane fractions of the adrenal gland cortex (bovine)

Adrenal gland cortices from cattle (AGCs), which have been freshly removed and carefully freed from gland medulla, are comminuted in sucrose solution (0.32M) with the aid of an Ultra-Turrax (Janke & Kunkel , Staufen i.B.) to give a coarse membrane homogenate and partially purified to give membrane fractions in two centrifugation steps.

The receptor binding investigations are carried out on partially purified membrane fractions of bovine AGC using radioactive angiotensin II in an assay volume of 0.25 ml, which specifically contains the partially purified membranes (50–80 µg), $^3$H-angiotensin II (3–5 nM), test buffer solution (50 mM Tris, pH 7.2, 5 mM $MgCl_2$) and the substances to be investigated. After an incubation period of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM Tris/ HCl, pH 7.4, 5% PEG 6000). The raw data were analysed using computer programs to give $K_i$ or $IC_{50}$ values ($K_i$: $IC_{50}$ values corrected for the radioactivity used: $IC_{50}$ values: concentration at which the substance to be investigated causes a 50% inhibition of the specific binding of the radioligand).

Investigation of the inhibition of the proliferation of smooth muscle cells by the compounds according to the invention To determine the antiproliferative action of the compounds, smooth muscle cells are used which are obtained from the aortas of rats by the media explant technique [R. Ross, J. Cell, Biol. 50, 172, 1971]. The cells are inoculated into suitable culture dishes, as a rule 96-hole plates, and cultured at 37° C. in 5% $CO_2$ for 2–3 days in medium 199 containing, 7.5% FCS and 7.5% NCS, 2mM L-glutamine and 15 mM HEPES, pH 7.4. The cells are then synchronized for 2–3 days by withdrawal of serum and then stimulated into growth using se or other factors. Test compounds are simultaneously added. After 16–20 hours, 1 μCi $^3$H-thymidine is added and after a further 4 hours the incorporation of this substance into the TCA-precipitable DNA of the cells is determined. To determine the IC$_{50}$ values, the active compound concentration is calculated which, on sequential dilution of the active compound, causes semi-maximum inhibition of the thymidine incorporation produced by 10% FCS.

TABLE A

| Ex. No. | IC$_{50}$[nM] |
|---|---|
| 27 | 580 |
| 30 | 0.1 |
| 32 | 2.0 |
| 50 | 0.9 |

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents.

In this case the therapeutically active compound should in each case be present in a concentration of about 0.5 to 90% by weight of the total mixture, i.e. in amounts which are sufficient in order to reach the dosage range indicated.

The formulations are prepared, for example, by extending the active compounds using solvents and/or excipients, if appropriate using emulsifiers and/or dispersants, where, for example, in the case of the use of water as a diluent organic solvents can optionally be used as auxiliary solvents.

Administration is carried out in a customary manner, preferably orally or parenterally, in particular perlingually or intravenously.

In the case of parenteral administration, solutions of the active compound using suitable liquid excipient materials can be employed.

In general, it has proven advantageous in the case of intravenous administration to administer amounts from about 0.001 to 1 mg/kg, preferably about 0.01 to 0.5 mg/kg, of body weight to obtain effective results, and in the case of oral administration the dose is about 0.01 to 20 mg/kg, preferably 0.1 to 10 mg/kg, of body weight.

In spite of this, it may possibly be necessary to depart from the amounts mentioned, depending on the body weight or the type of administration route, on individual behaviour towards the medicament, the manner of its formulation and the time or interval at which administration takes place. Thus, in some cases it may be sufficient to manage with less than the abovementioned minimum amount, while in other cases the upper limit mentioned must be-exceeded. In the case of the administration of larger amounts, it may be advisable to divide these into several individual doses over the course of the day.

Eluent mixtures
  A Petroleum ether: ethyl acetate=1:1
  B Dichloromethane: methanol=50:1
  C Petroleum ether: ethyl acetate=5:1
  D Dichloromethane
  E Petroleum ether: dichloromethane=3:1
  F Dichloromethane: methanol=20:1
  G Dichloromethane: methanol=10:1
  H Dichloromethane: ethyl acetate=1:1
  I Dichloromethane: ethyl acetate=2:1
  J Dichloromethane: methanol: aq. conc. ammonia= 200:20:1
  K Petroleum ether: ethyl acetate=4:1
  L Dichloromethane: ethyl acetate=10:1
  M Petroleum ether: ethyl acetate=10:1
  N Dichloromethane: methanol=7:1

Starting Compounds

EXAMPLE I trans-6-(4-Tolyl)-cyclohex-3-ene-1-carboxylic acid

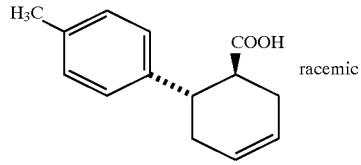

275 g (1.695 mol) of 3-E-(4-tolyl)acrylic acid (commercially available) is reacted at about 200° C. and about 20 bar for 22 h according to a known process (Eur. J. Med. Chem. 11, 493 (1976)) in 480 ml of toluene with 580 ml of 1,3-butadiene (measured in condensed form) with the addition of 3 g of hydroquinone. The crude mixture is diluted with toluene and extracted with 0.5M aqueous sodium hydroxide solution. The aqueous phases are then acidified with 1M hydrochloric acid and extracted with ether. The ethereal solutions are dried with sodium sulphate, evaporated and again dissolved in toluene. After boiling with 5 g of active carbon for 15 minutes, the mixture is filtered off hot with suction and the solvent is evaporated down to about 120–160 ml; 124 g (573 mmol) of product crystallize out at 0°–40° C. The filtrate is concentrated somewhat further and cooled again for further crystallization. On repeating this process, a total of a further 42 g (194 mmol) of product are obtained.

R$_f$=0.39 (dichloromethane: methanol=10:1).

EXAMPLE II trans-2-(4-Tolyl)-cyclohexane-1-carboxylic acid

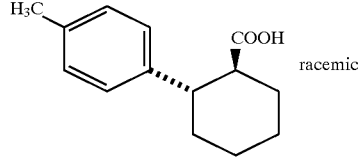

155 g (717 mmol) of the compound from Example I are dissolved in 1 l of methanol and reacted on 10 g of palladium (10% on animal carbon) at 20° C. and a hydrogen atmosphere of about 1 bar. After a reaction time of a total of 16 h, the catalyst is filtered off and the solvent is evaporated-finally in vacuo.

Yield: 153 g (701 mmol)

R$_f$=0.38 (dichloromethane: methanol=10:1)

EXAMPLE III tert-Butyl trans-2-(4-tolyl)-cyclohexane-1-carboxylate

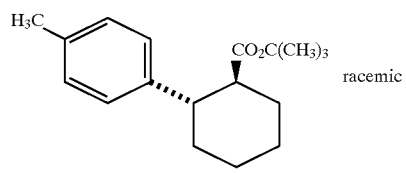
racemic

Method A 45.8 g (184 mmol) of the compound from Example II are dissolved in 600 ml of toluene and reacted under reflux with 49.5 ml (387 mmol) of oxalyl chloride. After 2 h, the solvent is evaporated with excess reagent; for this purpose the crude carbonyl chloride must optionally be repeatedly taken up in toluene and concentrated in a rotary evaporator one more time. The product thus obtained is dissolved in 500 ml of tetrahydrofuran, stirred with 24.8 g (221 mmol) of potassium tert-butoxide at 0° C. and subsequently stirred for 20 h (at 20° C.). Water and ether are then added and the mixture is extracted several times. The organic phase is dried with sodium sulphate and evaporated, and the residue is purified by chromatography on silica gel 60 (Merck, petroleum ether: ethyl acetate=20:1).

Yield: 39.6 g (130 mmol)

$R_f$=0.47 (petroleum ether: ethyl acetate=10:1)

Method B 20.0 g (91.6 mmol) of the compound from Example II are suspended in 7 ml of conc. sulphuric acid in 100 ml of ether and treated at −30° C. with 80 ml (713 mmol) of isobutene (pressure apparatus). The mixture is warmed to 20° C. in the closed vessel and reacted for 20 hours. It is then cooled again to −30° C., the apparatus is opened and the reaction mixture is stirred into 300 ml of 3M sodium hydroxide solution/400 ml of ether at 20° C. The aqueous phase is reextracted with ether, and the organic solution is dried with sodium sulphate and evaporated.

Yield: 23.3 g (84.9 mmol).

EXAMPLE IV tert-Butyl trans-2-(4-bromomethylphenyl)-cyclohexane-1-carboxylate

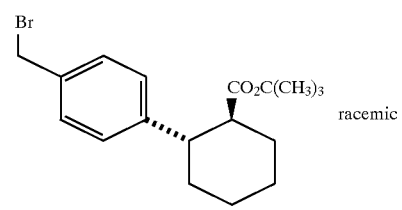
racemic 11.70 g (42.6 mmol) of the compound from Example III are reacted under reflux in 100 ml of tetrachloromethane with 7.59 g (42.6 mmol) of N-bromosuccinimide and 1.4 g of azobisisobutyronitrile. After a reaction time of 4 h, the mixture is cooled, the succinimide precipitate obtained is filtered off with suction and the filtrate is evaporated.

Yield: 14.2 g (40.2 mmol)

$R_f$=0.48 (petroleum ether: ethyl acetate=10:1)

EXAMPLE V 4,6-Dimethyl-2-hydrazino-pyridine

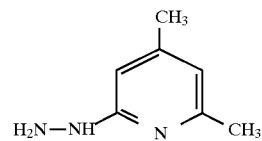

37.0 g (260 mmol) of 2-chloro-4,6-dimethyl-pyridine (US 3,632,807) are boiled for 15 hours under reflux with 67 ml of hydrazine hydrate in 200 ml of diethylene glycol. After cooling to room temperature, the mixture is extracted with water and ether/dichloromethane, and the organic phases are dried with sodium sulphate and evaporated. The crude product can be directly reacted further. $R_f$=0.18 (dichloromethane: methanol=10:1)

EXAMPLE VI 2,4-Dimethyl-5,6,7,8-tetrahydro-α-carboline 1.08 g (7.7 mmol) of the compound from Example V are stirred at 20° C. with 0.86 ml (8.3 mmol) of cyclohexanone, and the red hydrazone obtained after one hour is reacted further without purification by boiling it under reflux for 20 hours in 30 ml of diethylene glycol. On cooling to −10° C., a precipitate deposits, which is filtered off with suction and washed with a little cooled methanol. After drying the substance in a high vacuum over phosphorus pentoxide, 0.32 (1.6 mmol) of product is obtained.

$R_f$=0.41 (petroleum ether: ethyl acetate=1:1)

The compounds shown in Table I are prepared in analogy to the procedure of Example VI:

TABLE I

| | | $R_f$ (eluent) |
|---|---|---|
| Ex. No. VII | | 0.31 (A) |
| Ex. No. VIII | | 0.35 (A) |

EXAMPLE IX
trans-2-(4-Tolyl)-cyclohexane-1-carbonitrile

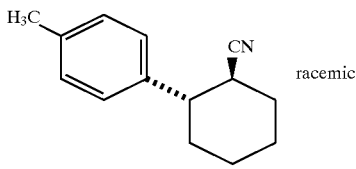

racemic 100.0 g (458.0 mmol) of the compound from Example II are reacted in 1 l of dichloromethane at boiling point with 84.3 g (595.5 mmol) of chlorosulphonyl isocyanate in 100 ml of dichloromethane for 1 h. 72 ml (938.9 mmol) of N,N-dimethylformamide are then added dropwise to the cooling reaction mixture and it is stirred for 18 h. The mixture is poured onto 350 g of ice, and the phases are separated after melting and extracted with dichloromethane. The organic phases dried with potassium carbonate are evaporated and the residue is distilled. 57.8 g (290.2 mmol) of product are obtained.

Boiling point: 122°–131° C. (0.2 mbar)
$R_f$=0.81 (dichloromethane)

EXAMPLE X
5-[trans-2-(4-Tolyl)-cyclohex-1-yl]tetrazole

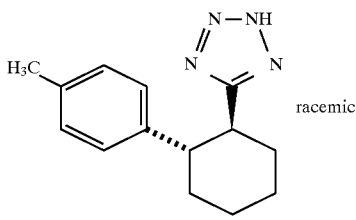

racemic 15.34 g (69.6 mmol) of the compound from Example IX are reacted at boiling heat in 230 ml of anhydrous N,N-dimethylformamide with 22.6 g (348 mmol) of sodium azide and 47.9 g (348 mmol) of triethylammonium chloride under nitrogen. After 20 h, the mixture is poured after cooling into ether and 1M sulphuric acid, and the organic phase is washed with 1M sulphuric acid and then extracted with 10% strength sodium hydroxide solution. The aqueous phase is adjusted to pH=1.5 at 0° C. using 1M hydrochloric acid and the precipitate obtained is filtered off with suction, washed with water and dried in a high vacuum over phosphorus pentoxide and sodium hydroxide.

Yield: 11.2 g (46.2 mmol)
$R_f$=0.23 (dichloromethane: methanol=20:1)

EXAMPLE XI
5-[trans-2-(4-Tolyl)-cyclohex-1-yl]-2-triphenylmethyltetrazole

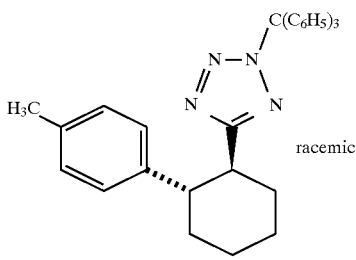

racemic 11.0 g (45.7 mmol) of the compound from Example X are reacted at 0° C. in 170 ml of dichloromethane with 13.4 g (48.2 mmol) of triphenylmethyl chloride and 7.57 ml (54.6 mmol) of triethylamine. The mixture is stirred for about 20 h while warming to room temperature and then extracted with ether and aqueous citric acid. The organic phases are dried with sodium sulphate and evaporated.

Yield: 22.1 g (45.5 mmol)
$R_f$=0.67 (petroleum ether: ethyl acetate=5:1)

EXAMPLE XII
5-[trans-2-(4-Bromomethylphenyl)-cyclohex-1-yl]-2-triphenylmethyl-tetrazole

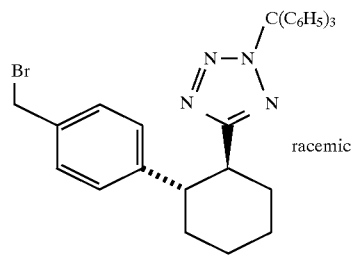

racemic 22.1 g (45.5 mmol) of the compound from Example XI are reacted under reflux in 300 ml of tetrachloromethane with 8.1 g (45.5 mmol) of N-bromosuccinimide and 0.3 g of azobisisobutyronitrile. After a reaction time of 3 hours, the mixture is cooled to room temperature and later to 0° C. and the precipitate is filtered off with suction. The filtrate is evaporated and a crude product (26.2 g) is obtained, which is reacted further without further working up.

$R_f$=0.47 (petroleum ether: ethyl acetate=10:1)

Preparation Examples

EXAMPLE 1
tert-Butyl trans-2-{4-[2,4-dimethyl-5,6,7,8-tetrahydro-α-carbolin-9-yl-methyl]phenyl}-cyclohexan-1-carboxylate

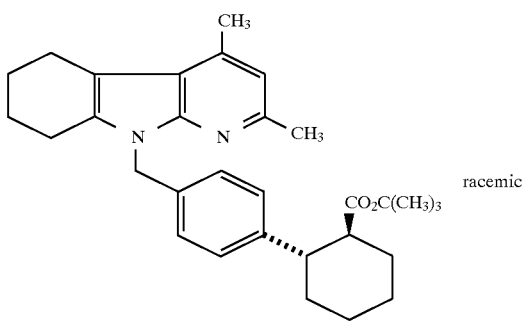

racemic 1.98 g (9.9 mmol) of the compound from Example VI are reacted (0° C.) in 70 ml of anhydrous dimethylformamide with 298 mg (9.9 mmol) of sodium hydride (80% strength, stabilized with paraffin) and after evolution of hydrogen is complete the mixture is stirred for 20 hours at 25° C. with 3.5 g (9.9 mmol) of the compound from Example IV. After addition of water, the mixture is extracted several times with ether, the combined organic phases are dried with sodium sulphate and the residue obtained on evaporation is chromatographed (silica gel 60, Merck, petroleum ether: ethyl acetate from 20:1 to 10:1).

Yield: 2.31 g (4.9 mmol)
$R_f$=0.49 (petroleum ether: ethyl acetate=10:1)

The compounds shown in Table 1 are prepared in analogy to the procedure of Example 1:

TABLE 1

[Structure: 4-(Z-CH2)-phenyl group attached to cyclohexane bearing T substituent, racemic, trans]

| Ex. No. | Z | T | R$_f$ (eluent) |
|---|---|---|---|
| 2 | β-carboline (9-methyl-β-carboline-1-yl, pyrido[3,4-b]indole) | —CO$_2$C(CH$_3$)$_3$ | 0.19 (B) |
| 3 | 5,6,7,8-tetrahydro-9-methyl-α-carboline analog (tetrahydropyrido[2,3-b]indole) | —CO$_2$C(CH$_3$)$_3$ | 0.61 (C) |
| 4 | 9-methyl-α-carboline (pyrido[2,3-b]indole) | —CO$_2$C(CH$_3$)$_3$ | 0.29 (D) |
| 5 | 9-methylcarbazole | —CO$_2$C(CH$_3$)$_3$ | 0.08 (E) |
| 6 | γ-carboline (9-methyl-pyrido[4,3-b]indole) | —CO$_2$C(CH$_3$)$_3$ | 0.41 (F) |
| 7 | 9-methyl-1,2,3,4-tetrahydrocarbazole | —CO$_2$C(CH$_3$)$_3$ | 0.62 (C) |
| 8 | 2,4-dimethyl-5,6,7,8-tetrahydro-9-methyl-α-carboline | tetrazole-N-C(C$_5$H$_3$)$_3$ (trityl-tetrazole) | 0.50 (C) |
| 9 | β-carboline (9-methyl, pyrido[3,4-b]indole isomer) | —CO$_2$C(CH$_3$)$_3$ | 0.12 (C) |
| 10 | 2,4-dimethyl-9-methyl-α-carboline | —CO$_2$C(CH$_3$)$_3$ | 0.73 (K) |

TABLE 1-continued

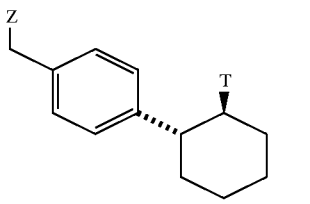

| Ex. No. | Z | T | $R_f$ (eluent) |
|---|---|---|---|
| 11 | 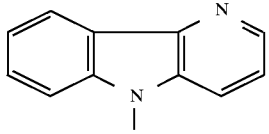 | $-CO_2C(CH_3)_3$ | 0.38 (A) |
| 12 | 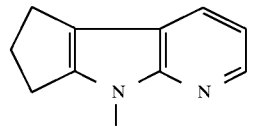 | $-CO_2C(CH_3)_3$ | 0.30 (M) |
| 13 | 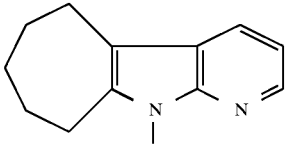 | $-CO_2C(CH_3)_3$ | 0.24 (M) |

EXAMPLE 14 trans-2-{4-[2,4-Dimethyl-5,6,7,8-tetrahydro-α-carbolin-9-yl-methyl]phenyl}-cyclohexane-l-carboxylic acid

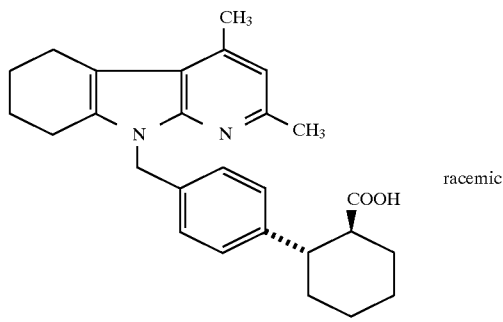

1.50 g (3.2 mmol) of the compound from example 14 are reacted at 20° C. in 10 ml of dioxane with 3 ml of 37% strength hydrochloric acid. After 3 hours, ether and water are added and the mixture is adjusted to pH=8 with sodium carbonate solution. The precipitate obtained is filtered off with suction, washed with water and ether and, after drying in a high vacuum over phosphorus pentoxide, purified by chromatography on silica gel 60 (Merck, dichloromethane:methanol=50:1).

Yield: 0.44 g (1.1 mmol)

$R_f$=0.63 (dichloromethane: methanol=10:1)

The compounds shown in Table 2 are prepared in analogy to the procedure of Example 14:

TABLE 2

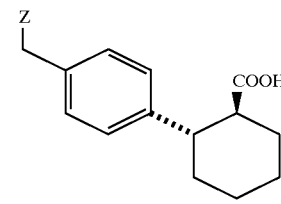

| Ex. No. | Z | $R_f$ (eluent) |
|---|---|---|
| 15 | 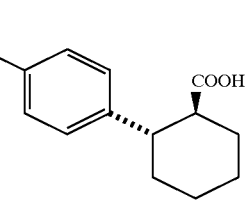 | 0.35 (L) |
| 16 | 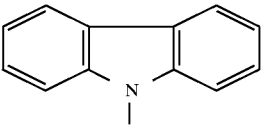 | 0.48 (G) |
| 17 | 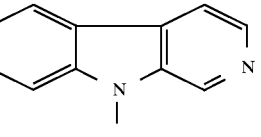 | 0.23 (G) |
| 18 | 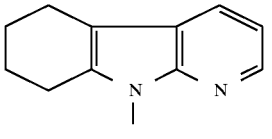 | 0.33 (G) |

TABLE 2-continued

| Ex. No. | Z | R_f (eluent) |
|---|---|---|
| 19 | tetrahydro-pyrido-pyridine (N-methyl) | 0.42 (G) |
| 20 | tetrahydro-pyrido-pyridine isomer | 0.41 (G) |
| 21 | tetrahydrocarbazole | 0.68 (A) |
| 22 | 2,4-dimethyl-tetrahydro-α-carboline | 0.43 (G) |
| 23 | tetrahydro-pyrido-pyridine | 0.45 (G) |
| 24 | cyclopenta-pyrido-pyridine | 0.37 (G) |
| 25 | cyclohepta-pyrido-pyridine | 0.42 (G) |

EXAMPLE 26 trans-2-{4-[2,4-Dimethyl-5,6,7,8-tetrahydro-α-carbolin-9-yl-methyl]phenyl}-N-[4-tolylsulfonyl]cyclohexane-1-carboxamide

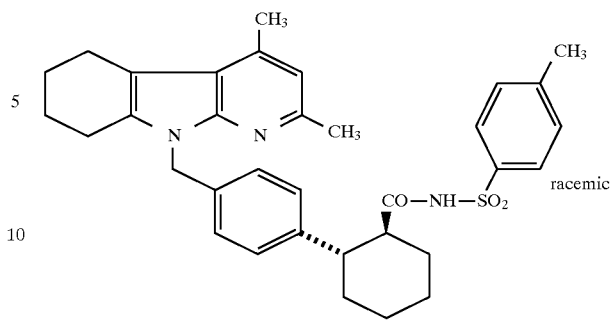

427 mg (1.03 mmol) of the compound from Example 14 are reacted at −20° C. in 20 ml of anhydrous tetrahydrofuran with 622 μl (4.51 mmol) of triethylamine and 87.2 μl (1.13 mmol) of mesyl chloride. After 2 hours, 500 mg (4.1 mmol) of 4-(N,N-dimethylamino)pyridine and 211 mg (1.23 mmol) of 4-toluenesulphonamide are added and the mixture is stirred for 18 hours while warming to 20° C. The mixture is poured into water and extracted several times with ether; the combined organic phases are dried with sodium sulphate, concentrated and purified on silica gel 60 (Merck, petroleum ether/ethyl acetate=2:1 to 1: 1).

Yield: 0.38 g (0.69 mmol)

$R_f$=0.46 (dichloromethane: methanol=10:1)

EXAMPLES 27 AND 28 trans-2-{4-[2,4-Dimethyl-5,6,7,8-tetrahydro-α-carbolin-9-yl-methyl]phenyl}-N((S)-phenylglycinol)cyclohexane-1-carboxamide

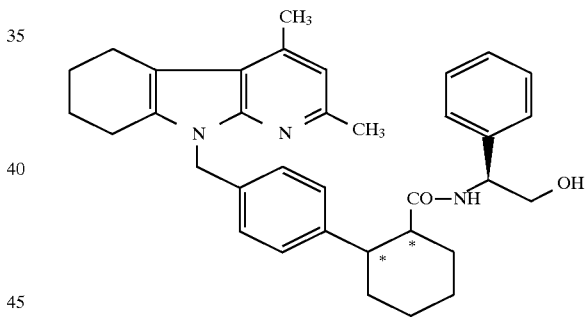

* trans 427 mg (1.03 mmol) of the compound from Example 14 are reacted at −30° C. in 20 ml anhydrous tetrahydrofuran with 288 μl (2.10 mmol) of triethylamine and 87 μl (1.13 mmol) of mesyl chloride. After 30 minutes, 169 mg (1.23 mmol) of (S)-phenylglycinol and 126 mg (1.03 mmol) of 4-(N,N-dimethylamino)pyridine are added in 15 ml of anhydrous tetrahydrofuran and the mixture is stirred for 20 hours while warming to 20° C. Water is added and the mixture is extracted several times with ether. The organic phase is dried with sodium sulphate and evaporated. The crude product is then purified on silica gel 60 (Merck, petroleum ether: ethyl acetate 2:1 to 1:1).

Yields:

110 mg (0.21 mmol) of diastereomer A (Example 27);

$R_f$=0.29 (A) 40 mg (0.07 mmol) of diastereomer B (Example 28);

$R_f$=0.15 (A)

The compounds shown in Table 3 are prepared in analogy to the procedures of Examples 27 and 28:

TABLE 3

| Ex. No. | Z | R | $R_f$ (eluent) |
|---|---|---|---|
| 29 | β-carboline (9H-pyrido[3,4-b]indole) | $C_6H_5$, CH(CH$_3$)CH$_2$OH | 0.52 (G) |
| 30 | β-carboline isomer | $C_6H_5$, CH(CH$_3$)CH$_2$OH | 0.47 (G) |
| 31 | β-carboline isomer | $C_6H_5$, CH(CH$_3$)CH$_2$OH | 0.50 (H) |
| 32 | α-carboline (9H-pyrido[2,3-b]indole) | $C_6H_5$, CH(CH$_3$)CH$_2$OH | 0.34 (H) |
| 33 | γ-carboline | $C_6H_5$, CH(CH$_3$)CH$_2$OH | 0.21 (G) |
| 34 | γ-carboline isomer | $C_6H_5$, CH(CH$_3$)CH$_2$OH | 0.17 (G) |
| 35 | carbazole | $C_6H_5$, CH(CH$_3$)CH$_2$OH | 0.64 (I) |
| 36 | carbazole | $C_6H_5$, CH(CH$_3$)CH$_2$OH | 0.37 (I) |
| 37 | tetrahydro-α-carboline | $C_6H_5$, CH(CH$_3$)CH$_2$OH | 0.29 (A) |

* = trans

TABLE 3-continued

[Structure: Z-CH2-C6H4-cyclohexane(trans)-CO-NH-R]  * = trans

| Ex. No. | Z | R | R$_f$ (eluent) |
|---|---|---|---|
| 38 | 1,2,3,4-tetrahydro-β-carboline-pyridine fused | C$_6$H$_5$-CH(CH$_3$)-CH$_2$OH | 0.15 (A) |
| 39 | α-carboline | C$_6$H$_5$-CH(CH$_3$)-CH$_2$OH | 0.23 (A) |
| 40 | α-carboline | C$_6$H$_5$-CH(CH$_3$)-CH$_2$OH | 0.14 (H) |
| 41 | 1,2,3,4-tetrahydrocarbazole | C$_6$H$_5$-CH(CH$_3$)-CH$_2$OH | 0.36 (H) |
| 42 | 1,2,3,4-tetrahydrocarbazole | C$_6$H$_5$-CH(CH$_3$)-CH$_2$OH | 0.28 (H) |
| 43 | 2,4-dimethyl-α-carboline | C$_6$H$_5$-CH(CH$_3$)-CH$_2$OH | 0.74 (J) |
| 44 | 2,4-dimethyl-α-carboline | C$_6$H$_5$-CH(CH$_3$)-CH$_2$OH | 0.55 (J) |
| 45 | 1,2,3,4-tetrahydro-α-carboline | C$_6$H$_5$-CH(CH$_3$)-CH$_2$OH | 0.49 (G) |

TABLE 3-continued

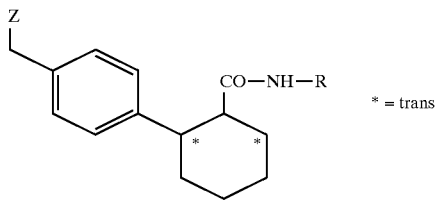
* = trans

| Ex. No. | Z | R | $R_f$ (eluent) |
|---|---|---|---|
| 46 | 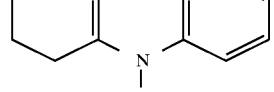 | C₆H₅ ⟋⟍OH (with CH₃) | 0.46 (G) |
| 47 | 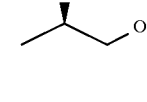 | C₆H₅ ⟋⟍OH | 0.86 (N) |
| 48 |  | C₆H₅ ⟋⟍OH | 0.72 (N) |
| 49 | 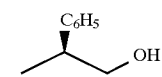 | C₆H₅ ⟋⟍OH | 0.51 (G) |
| 50 | 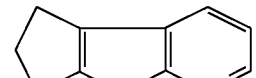 | C₆H₅ ⟋⟍OH | 0.49 (G) |

EXAMPLE 51

5-[trans-2{4-(2,4-Dimethyl-5,6,7,8-tetrahydro-α-carbolin-9-yl-methyl)-phenyl}-cyclohex-1-yl]tetrazole

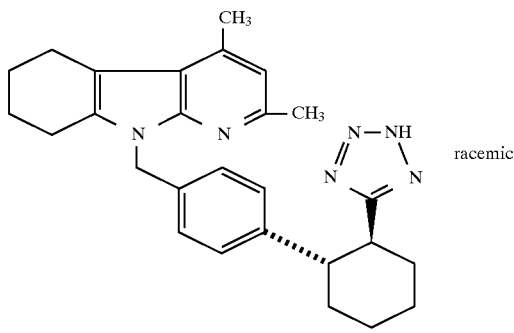
racemic 0.12 g (0.2 mmol) of the compound from Example 8 are dissolved in 3 ml of tetrahydrofuran and reacted for 2 hours at 20° C. with 0.5 ml of water and 0.5 ml of trifluoroacetic acid. Ether is then added, the mixture is extracted with aqueous sodium hydroxide solution (pH=13.5) and the aqueous phase is adjusted to pH=3–4 using 1M hydrochloric acid. The precipitate which deposits is filtered off with suction, washed with water and dried in a high vacuum over phosphorus pentoxide and sodium hydroxide.

Yield: 0.05 g (0.1 mmol)

$R_f$=0.38 (dichloromethane: methanol 20:1)

We claim:

1. A heterotricyclically substituted phenyl-cyclohexane-carboxylic acid derivative of the formula

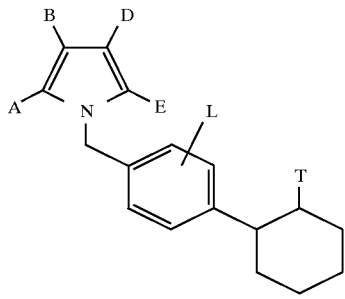

in which

A and B together form a radical of the formula

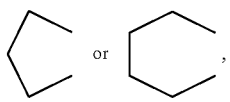

D and E together form a radical of the formula

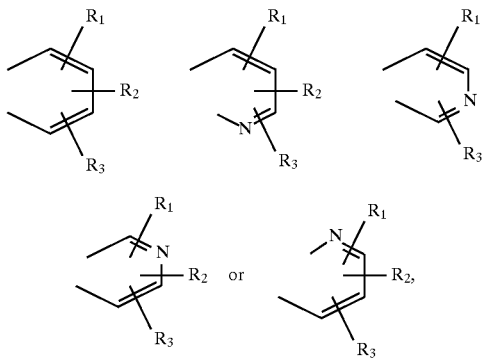

in which

R¹, R² and R³ are identical or different and denote hydrogen or aryl having 6 to 10 carbon atoms, which is optionally substituted by hydroxyl, halogen or trifluoromethyl or by straight-chain or branched alkyl or alkoxy in each case having up to 6 carbon atoms, or denote straight-chain or branched alkyl or alkenyl in each case having up to 8 carbon atoms, or denote cycloalkyl having 3 to 8 carbon atoms, or denote halogen, L represents hydrogen, halogen, nitro, hydroxyl, trifluoromethyl, trifluoromethoxy, straight-chain or branched alkyl, alkoxy or alkoxycarbonyl in each case having up to 6 carbon atoms, cyano or carboxyl, T represents a radical of the formula

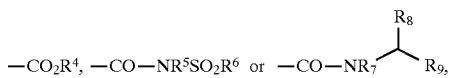

in which

R⁴ denotes hydrogen, straight-chain or branched alkyl having up to 8 carbon atoms, cycloalkyl having 3 to 7 carbon atoms or phenyl, R⁵ and R⁷ are identical or different and denote hydrogen or straight-chain or branched alkyl having up to 6 carbon atoms, R⁶ denotes trifluoromethyl or straight-chain or branched alkyl having up to 6 carbon atoms, or benzyl or phenyl, each of which is optionally substituted by straight-chain or branched alkyl having up to 6 carbon atoms, R⁸ denotes aryl having 6 to 10 carbon atoms, which is optionally substituted up to 2 times by identical or different substituents from the group consisting of halogen, hydroxyl, straight-chain or branched alkyl, alkoxy or alkoxycarbonyl in each case having up to 6 carbon atoms carboxyl, phenoxy and $C_3$–$C_6$-cycloalkoxy, R⁹ denotes a group of the formula —$CH_2$—$OR^{10}$, —$CO_2R^{11}$, —CO—$NR^{12}R^{13}$ or pyridyl, in which R¹⁰ denotes hydrogen or straight-chain or branched alkyl having up to 8 carbon atoms, R¹¹ denotes hydrogen or straight-chain or branched alkyl having up to 8 carbon atoms, or phenyl or cycloalkyl having 3 to 6 carbon atoms, R¹² and R¹³ are identical or different and denote hydrogen or straight-chain or branched alkyl having up to 8 carbon atoms, or phenyl, or T represents tetrazolyl, which is optionally substituted by straight-chain or branched alkyl having up to 4 carbon atoms or by the triphenylmethyl group, or a physiological accepted salt thereof.

2. A heterotricyclically substituted phenyl-cyclohexane-carboxylic acid derivative according to claim 1, in which R¹, R² and R³ are identical or different and denote hydrogen or phenyl which is optionally substituted by hydroxyl, fluorine, chlorine, bromine, or trifluoromethyl or by straight-chain or branched alkyl or alkoxy in each case having up to 4 carbon atoms, or denote straight-chain or branched alkyl or alkenyl in each case having up to 6 carbon atoms, or denote cyclopropyl, cyclobutyl, cyclopentyl, cyclohexyl or cycloheptyl, or denote fluorine, chlorine or bromine, L represents hydrogen, fluorine, chlorine, bromine, trifluoromethyl, carboxyl or straight-chain or branched alkyl, alkoxy or alkoxycarbonyl in each case having up to 4 carbon atoms, R⁴ denotes hydrogen, straight-chain or branched alkyl having up to 6 carbon atoms, cyclopropyl, cyclopentyl, cyclohexyl or phenyl, R⁵ and R⁷ are identical or different and denote hydrogen or straight-chain or branched alkyl having up to 4 carbon atoms, R⁶ denotes trifluoromethyl or straight-chain or branched alkyl having up to 4 carbon atoms, or benzyl or phenyl, each of which is optionally substituted by straight-chain or branched alkyl having up to 4 carbon atoms, R⁸ denotes phenyl which is optionally substituted by fluorine, chlorine, bromine, hydroxyl, straight-chain or branched alkyl, alkoxy or alkoxycarbonyl in each case having up to 4 carbon atoms, carboxyl or phenoxy, R⁹ denotes a group of the formula —$CH_2$—$OR^{10}$, —$CO_2R^{11}$, —CO—$NR^{12}R^{13}$ or pyridyl, in which R¹⁰ denotes hydrogen or straight-chain or branched alkyl having up to 6 carbon atoms, R¹¹ denotes hydrogen, straight-chain or branched alkyl having up to 6 carbon atoms, phenyl, cyclopropyl, cyclopentyl or cyclohexyl, and R¹² and R¹³ are identical or different and denote hydrogen, straight-chain or branched alkyl having up to 6 carbon atoms, cyclopropyl, cyclopentyl, cyclohexyl or phenyl.

3. A heterotricyclically substituted phenyl-cyclohexane-carboxylic acid derivative according to claim 1, in which $R^1$, $R^2$ and $R^3$ are identical or different and denote hydrogen, methyl, fluorine, chlorine, bromine, L represents hydrogen, fluorine, chlorine, bromine, trifluoromethyl, trifluoromethoxy or methyl, $R^4$ denotes hydrogen, straight-chain or branched alkyl having up to 4 carbon atoms, cyclopropyl, cyclopentyl, cyclohexyl or phenyl, $R^5$ and $R^7$ are identical or different and denote hydrogen, bromine or methyl, $R^6$ denotes trifluoromethyl or methyl, ethyl, benzyl, p-tolyl or phenyl, $R^8$ denotes phenyl which is optionally substituted by fluorine, chlorine, bromine, hydroxyl, straight-chain or branched alkyl, alkoxy or alkoxycarbonyl in each case having up to 3 carbon atoms, carboxyl or phenoxy, $R^9$ denotes a group of the formula $-CH_2-OR^{10}$, $-CO_2R^{11}$, $-CO-NR^{12}R^{13}$ or pyridyl, in which $R^{10}$ denotes hydrogen or straight-chain or branched alkyl having up to 4 carbon atoms, $R^{11}$ denotes hydrogen, straight-chain or branched alkyl having up to 4 carbon atoms, phenyl, cyclopropyl, cyclopentyl or cyclohexyl, and $R^{12}$ and $R^{13}$ are identical or different and denote hydrogen, straight-chain or branched alkyl having up to 4 carbon atoms, cyclopropyl, cyclopentyl, cyclohexyl or phenyl.

4. A heterotricyclically substituted phenyl-cyclohexane-carboxylic acid derivative according to claim 1, in which $R^1$, $R^2$ and $R^3$ are identical or different and denote hydrogen, bromine or methyl, L represents hydrogen, $R^4$ denotes hydrogen or straight-chain or branched alkyl having up to 4 carbon atoms, $R^5$ and $R^7$ denote hydrogen, $R^6$ denotes trifluoromethyl, methyl or p-tolyl, $R^8$ denotes phenyl, and $R^9$ denotes a group of the formula $-CH_2-OH$.

5. A heterotricyclically substituted phenyl-cyclohexane-carboxylic acid derivative of the formula in which A and B together form a radical of the formula D and E together form a radical of the formula in which $R^1$, $R^2$ and $R^3$ are identical or different and denote hydrogen or aryl having 6 to 10 carbon atoms, which is optionally substituted by hydroxyl, halogen or trifluoromethyl or by straight-chain or branched alkyl or alkoxy in each case having up to 6 carbon atoms, or denote straight-chain or branched alkyl or alkenyl in each case having up to 8 carbon atoms, or denote cycloalkyl having 3 to 8 carbon atoms, or denote halogen, L represents hydrogen, halogen, nitro, hydroxyl, trifluoromethyl, trifluoromethoxy, straight-chain or branched alkyl, alkoxy or alkoxycarbonyl in each case having up to 6 carbon atoms, cyano or carboxyl, $R^7$ denotes hydrogen or straight-chain or branched alkyl having up to 6 carbon atoms, $R^8$ denotes aryl having 6 to 10 carbon atoms, which is optionally substituted up to 2 times by identical or different substituents from the group consisting of halogen, hydroxyl, straight-chain or branched alkyl, alkoxy or alkoxycarbonyl in each case having up to 6 carbon atoms, carboxyl or phenoxy and $C_3$-$C_6$-cycloalkoxy, $R^9$ denotes a group of the formula $-CH_2-OR^{10}$, $-CO_2R^{11}$, $-CO-NR^{12}R^{13}$ or pyridyl, in which $R^{10}$ denotes hydrogen or straight-chain or branched alkyl having up to 8 carbon atoms, $R^{11}$ denotes hydrogen, straight-chain or branched alkyl having up to 8 carbon atoms, or phenyl or cycloalkyl having 3 to 6 carbon atoms, $R^{12}$ and $R^{13}$ are identical or different and denote hydrogen, straight-chain or branched alkyl having up to 8 carbon atoms or phenyl, or physiological accepted salt thereof.

6. A heterotricyclically substituted phenyl-cyclohexane-carboxylic acid derivative according to claim 5, in which $R^1$, $R^2$ and $R^3$ are identical or different and denote hydrogen or phenyl which is optionally substituted by hydroxyl, fluorine, chlorine, bromine, or trifluoromethyl or by straight-chain or branched alkyl or alkoxy in each case having up to 4 carbon atoms, or denote straight-chain or branched alkyl or alkenyl in each case having up to 6 carbon atoms, or denote cyclopropyl, cyclobutyl, cyclopentyl, cyclohexyl or cycloheptyl, or denote fluorine, chlorine or bromine, L represents hydrogen, fluorine, chlorine, bromine, trifluoromethyl, carboxyl or straight-chain or branched alkyl, alkoxy or alkoxycarbonyl in each case having up to 4 carbon atoms, $R^7$ are identical or different and denote hydrogen or straight-chain or branched alkyl having up to 4 carbon atoms, $R^8$ denotes phenyl which is optionally substituted by fluorine, chlorine, bromine, hydroxyl, straight-chain or branched alkyl, alkoxy or alkoxycarbonyl in each case having up to 4 carbon atoms, carboxyl or phenoxy, $R^9$ denotes a group of the formula —$CH_2$—$OR^{10}$, —$CO_2R^{11}$, —CO—$NR^{12}R^{13}$ or pyridyl, in which $R^{10}$ denotes hydrogen or straight-chain or branched alkyl having up to 6 carbon atoms, $R^{11}$ denotes hydrogen, straight-chain or branched alkyl having up to 6 carbon atoms, phenyl, cyclopropyl, cyclopentyl or cyclohexyl, and $R^{12}$ and $R^{13}$ are identical or different and denote hydrogen, straight-chain or branched alkyl having up to 6 carbon atoms, cyclopropyl, cyclopentyl, cyclohexyl or phenyl.

7. A heterotricyclically substituted phenyl-cyclohexane-carboxylic acid derivative according to claim 5, in which $R^1$, $R^2$ and $R^3$ are identical or different and denote hydrogen methyl, fluorine, chlorine, bromine, L represents hydrogen, fluorine, chlorine, bromine, trifluoromethyl, trifluoromethoxy or methyl, $R^7$ are identical or different and denotes hydrogen, bromine or methyl, $R^8$ denotes phenyl which is optionally substituted by fluorine, chlorine, bromine, hydroxyl, straight-chain or branched alkyl, alkoxy or alkoxycarbonyl in each case having up to 3 carbon atoms, carboxyl or phenoxy, $R^9$ denotes a group of the formula —$CH_2$—$OR^{10}$, —$CO_2R^{11}$, —CO—$NR^{12}R^{13}$ or pyridyl, in which $R^{10}$ denotes hydrogen or straight-chain or branched alkyl having up to 4 carbon atoms, $R^{11}$ denotes hydrogen, straight-chain or branched alkyl having up to 4 carbon atoms, phenyl, cyclopropyl, cyclopentyl or cyclohexyl, and $R^{12}$ and $R^{13}$ are identical or different and denote hydrogen, straight-chain or branched alkyl having up to 4 carbon atoms, cyclopropyl, cyclopentyl, cyclohexyl or phenyl.

8. A heterotricyclically substituted phenyl-cyclohexane-carboxylic acid derivative according to claim 5, in which $R^1$, $R^2$ and $R^3$ are identical or different and denote hydrogen, bromine and methyl, L represents hydrogen, $R^7$ denotes hydrogen, $R^8$ denotes phenyl, and $R^9$ denotes a group of the formula —$CH_2$—OH.

9. A heterotricyclically substituted phenyl-carboxylic acid derivative according to claim 1, wherein A and B together form a radical of the formula

10. A heterotricyclically substituted phenyl-carboxylic acid derivative according to claim 5, wherein A and B together form a radical of the formula

11. A heterotricyclically substituted phenyl-carboxylic acid derivative according to claim 3, wherein A and B together form a radical of the formula

12. A heterotricyclically substituted phenyl-carboxylic acid derivative according to claim 7, wherein A and B together form a radical of the formula

13. A heterotricyclically substituted phenyl-carboxylic acid derivative according to claim 5, wherein A and B together form a radical of the formula

14. A heterotricyclically substituted phenyl-carboxylic acid derivative according to claim 1, wherein A and B together form a radical of the formula

15. A heterotricyclically substituted phenyl-carboxylic acid derivative according to claim 7, wherein A and B together form a radical of the formula

16. A heterotricyclically substituted phenyl-carboxylic acid derivative according to claim 3, wherein A and B together form a radical of the formula

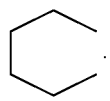

or a salt thereof.

17. A composition for the treatment of arterial hypertension and atherosclerosis comprising an amount effective therefore of a compound or salt thereof according to claim 1 and a pharmacologically acceptable diluent.

18. The method of treating arterial hypertension and atherosclerosis in a patient in need thereof which comprises administering to such patient an amount effective therefore of a compound or salt thereof according to claim 1.

* * * * *

UNITED STATES PATENT AND TRADEMARK OFFICE
CERTIFICATE OF CORRECTION

PATENT NO : 5,834,481
DATED : November 10, 1998
INVENTOR(S): Muller, et al.

It is certified that error appears in the above-identified patent and that said Letters Patent is hereby corrected as shown below:

Col. 33, line 28   Delete " 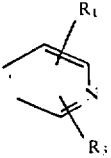 " and substitute

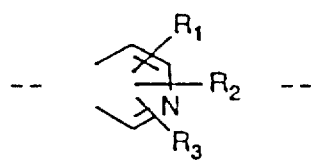

Col. 39, line 3   Delete " or a salt thereof "

Signed and Sealed this

Eighth Day of February, 2000

Attest:

Q. TODD DICKINSON

Attesting Officer

Commissioner of Patents and Trademarks